(12) United States Patent  
Christensen

(10) Patent No.: US 7,520,904 B2
(45) Date of Patent: *Apr. 21, 2009

(54) PROSTHETIC FOOT WITH AN ADJUSTABLE ANKLE AND METHOD

(75) Inventor: Roland J. Christensen, Fayette, UT (US)

(73) Assignee: Freedom Innovations, LLC, Irvine, CA (US)

( * ) Notice: Subject to any disclaimer, the term of this patent is extended or adjusted under 35 U.S.C. 154(b) by 478 days.

This patent is subject to a terminal disclaimer.

(21) Appl. No.: 11/254,621

(22) Filed: Oct. 19, 2005

(65) Prior Publication Data

US 2006/0041321 A1 Feb. 23, 2006

Related U.S. Application Data

(63) Continuation-in-part of application No. 10/970,679, filed on Oct. 20, 2004, now Pat. No. 7,462,201, which is a continuation-in-part of application No. 10/690,941, filed on Oct. 21, 2003, now Pat. No. 6,966,933.

(51) Int. Cl.
*A61F 2/64* (2006.01)
*A61F 2/48* (2006.01)

(52) U.S. Cl. .......................... 623/47; 623/24

(58) Field of Classification Search .................. 623/24, 623/47–56; 318/568.12
See application file for complete search history.

(56) References Cited

U.S. PATENT DOCUMENTS

| | | | |
|---|---|---|---|
| 42,799 A | 5/1864 | Shepard | |
| 92,031 A | 6/1869 | Foster | |
| 292,800 A | 2/1884 | Furrer | |
| 497,026 A * | 5/1893 | Judson | 623/52 |
| 1,001,641 A | 8/1911 | Harrison | |
| 1,289,580 A | 12/1918 | Vincenti | |
| 1,779,765 A | 10/1930 | Eichhorn | |
| 1,996,874 A | 4/1935 | Mascau | |
| 2,036,830 A | 4/1936 | Rowley | |
| 2,379,538 A | 7/1945 | Meierhofer | |
| 2,443,356 A | 6/1948 | Mathis | |
| 2,453,969 A | 11/1948 | Carter | |
| 2,470,480 A | 5/1949 | Fogg | |
| 2,570,735 A | 10/1951 | Weise | |

(Continued)

FOREIGN PATENT DOCUMENTS

BR 9304225 A 7/1995

(Continued)

*Primary Examiner*—Bruce E Snow
(74) *Attorney, Agent, or Firm*—Thorpe North & Western

(57) ABSTRACT

A prosthetic foot with an adjustable ankle includes an upper portion coupled to a socket of an amputee. A lower portion is adjustably coupled to the upper portion, and is attached to a foot member with heel and toe sections. A movable coupling is disposed between the upper and lower portions, and includes a displacement member slidably coupled to a displacement track. The movable coupling allows the toe section to pivot downward and the heel section to simultaneously displace forward. The adjustable ankle can be adjusted with an actuator coupled to a tractor bolt coupled between the upper and lower portions. A sensor is associated with the upper portion or the lower portion to sense frequency of contact, force of contact, or orientation of the upper portion or the lower portion, and to output a corresponding output signal.

17 Claims, 7 Drawing Sheets

U.S. PATENT DOCUMENTS

| | | | |
|---|---|---|---|
| 2,617,115 A | 11/1952 | Ellery | |
| 2,640,200 A | 6/1953 | Wisbrun | |
| 2,843,853 A | 6/1958 | Mauch | |
| 3,206,235 A | 9/1965 | Albinson et al. | |
| 3,548,420 A | 12/1970 | Spence | |
| 3,551,914 A | 1/1971 | Woodall | |
| 3,754,286 A | 8/1973 | Ryan | |
| 3,858,379 A | 1/1975 | Graves et al. | |
| 3,871,032 A | 3/1975 | Karas | |
| 3,874,004 A | 4/1975 | May | |
| 3,906,552 A | 9/1975 | Weber | |
| 3,920,610 A | 11/1975 | Wagner | |
| 3,956,775 A | 5/1976 | Moore | |
| 3,982,280 A | 9/1976 | Asbelle et al. | |
| 4,089,072 A | 5/1978 | Glabiszewski | |
| 4,328,594 A | 5/1982 | Campbell et al. | |
| 4,442,554 A | 4/1984 | Copes | |
| 4,499,613 A * | 2/1985 | Yarrow | 623/48 |
| 4,506,395 A | 3/1985 | Haupt | |
| 4,547,913 A | 10/1985 | Phillips | |
| 4,606,332 A | 8/1986 | Gibson | |
| 4,636,220 A | 1/1987 | Ziegelmeyer | |
| 4,645,509 A | 2/1987 | Poggi et al. | |
| 4,676,800 A | 6/1987 | Chen | |
| 4,676,801 A | 6/1987 | Lundeen | |
| 4,721,510 A | 1/1988 | Cooper et al. | |
| 4,822,363 A | 4/1989 | Phillips | |
| 4,865,611 A | 9/1989 | Al-Turaiki | |
| 4,865,612 A | 9/1989 | Arbogast et al. | |
| 4,938,775 A | 7/1990 | Morgan | |
| 4,959,073 A | 9/1990 | Merlette | |
| 5,019,109 A | 5/1991 | Voisin | |
| 5,030,239 A | 7/1991 | Copes | |
| 5,037,444 A | 8/1991 | Phillips | |
| 5,062,859 A | 11/1991 | Naeder | |
| 5,112,356 A | 5/1992 | Harris et al. | |
| 5,116,383 A | 5/1992 | Shorter et al. | |
| 5,116,384 A | 5/1992 | Wilson et al. | |
| 5,156,632 A | 10/1992 | Wellershaus | |
| 5,181,932 A | 1/1993 | Phillips | |
| 5,181,933 A | 1/1993 | Phillips | |
| 5,217,500 A | 6/1993 | Phillips | |
| 5,219,365 A | 6/1993 | Sabolich | |
| 5,258,039 A | 11/1993 | Goh et al. | |
| 5,267,633 A | 12/1993 | Endo et al. | |
| 5,290,319 A | 3/1994 | Phillips | |
| 5,314,499 A | 5/1994 | Collier, Jr. | |
| 5,376,133 A | 12/1994 | Gramnas | |
| 5,376,139 A | 12/1994 | Pitkin | |
| 5,376,141 A | 12/1994 | Phillips | |
| 5,387,246 A | 2/1995 | Phillips | |
| 5,425,781 A | 6/1995 | Allard et al. | |
| 5,425,782 A | 6/1995 | Phillips | |
| 5,443,528 A | 8/1995 | Allen | |
| 5,443,529 A | 8/1995 | Phillips | |
| 5,458,656 A | 10/1995 | Phillips | |
| 5,464,441 A | 11/1995 | Phillips | |
| 5,482,513 A | 1/1996 | Wilson | |
| 5,486,209 A | 1/1996 | Phillips | |
| 5,507,838 A | 4/1996 | Chen | |
| 5,509,936 A | 4/1996 | Rappoport et al. | |
| 5,509,937 A | 4/1996 | Allard et al. | |
| 5,509,938 A | 4/1996 | Phillips | |
| 5,514,185 A | 5/1996 | Phillips | |
| 5,514,186 A | 5/1996 | Phillips | |
| 5,549,714 A | 8/1996 | Phillips | |
| 5,571,210 A | 11/1996 | Lindh | |
| 5,571,213 A | 11/1996 | Allen | |
| 5,593,455 A | 1/1997 | Phillips | |
| 5,593,456 A | 1/1997 | Merlette | |
| 5,593,457 A | 1/1997 | Phillips | |
| 5,653,767 A | 8/1997 | Allen et al. | |
| 5,653,768 A | 8/1997 | Kania | |
| 5,725,598 A | 3/1998 | Phillips | |
| 5,728,175 A | 3/1998 | Rincoe | |
| 5,728,176 A | 3/1998 | Phillips | |
| 5,728,177 A | 3/1998 | Phillips | |
| 5,746,774 A | 5/1998 | Kramer et al. | |
| 5,766,265 A | 6/1998 | Phillips | |
| 5,766,704 A | 6/1998 | Allen et al. | |
| 5,769,896 A | 6/1998 | Rosendahl et al. | |
| 5,776,205 A | 7/1998 | Phillips | |
| 5,779,735 A | 7/1998 | Molino | |
| 5,800,564 A | 9/1998 | Gelineau | |
| 5,800,565 A | 9/1998 | Biedermann | |
| 5,800,569 A | 9/1998 | Phillips | |
| 5,824,112 A | 10/1998 | Phillips | |
| 5,888,238 A | 3/1999 | Phillips et al. | |
| 5,893,891 A | 4/1999 | Zahedi | |
| 5,899,944 A | 5/1999 | Phillips | |
| 5,913,902 A | 6/1999 | Geible | |
| 5,944,760 A | 8/1999 | Christensen | |
| 5,957,981 A | 9/1999 | Gramnas | |
| 5,976,191 A | 11/1999 | Phillips | |
| 5,993,488 A | 11/1999 | Phillips | |
| 6,019,795 A | 2/2000 | Phillips | |
| 6,071,313 A | 6/2000 | Phillips | |
| 6,077,301 A | 6/2000 | Pusch | |
| 6,120,547 A | 9/2000 | Christensen | |
| 6,165,227 A | 12/2000 | Phillips | |
| 6,187,052 B1 | 2/2001 | Molino et al. | |
| 6,197,068 B1 | 3/2001 | Christensen | |
| 6,206,934 B1 | 3/2001 | Phillips | |
| 6,228,124 B1 | 5/2001 | Slemker et al. | |
| 6,241,776 B1 | 6/2001 | Christensen | |
| 6,254,643 B1 | 7/2001 | Phillips | |
| 6,261,324 B1 | 7/2001 | Merlette | |
| 6,280,479 B1 | 8/2001 | Phillips | |
| 6,290,730 B1 | 9/2001 | Pitkin et al. | |
| 6,306,178 B1 | 10/2001 | Kania et al. | |
| 6,402,790 B1 | 6/2002 | Celebi | |
| 6,406,500 B1 | 6/2002 | Phillips | |
| 6,443,993 B1 | 9/2002 | Koniuk | |
| 6,443,995 B1 | 9/2002 | Townsend et al. | |
| 6,514,293 B1 | 2/2003 | Jang et al. | |
| 6,562,075 B2 | 5/2003 | Townsend et al. | |
| 6,596,029 B1 | 7/2003 | Gramnas | |
| 6,602,295 B1 | 8/2003 | Doddroe et al. | |
| 6,663,673 B2 | 12/2003 | Chirstensen | |
| 6,676,708 B1 | 1/2004 | Laghi | |
| 6,793,683 B1 | 9/2004 | Laghi | |
| 6,869,451 B1 | 3/2005 | Laghi | |
| 6,875,241 B2 | 4/2005 | Christensen | |
| 6,966,933 B2 | 11/2005 | Christensen | |
| 2002/0133237 A1 | 9/2002 | Christensen | |
| 2003/0045944 A1 | 3/2003 | Mosler et al. | |
| 2005/0197717 A1 | 9/2005 | Ragnarsdottir et al. | |

FOREIGN PATENT DOCUMENTS

| | | |
|---|---|---|
| DE | 295807 | 12/1916 |
| EP | 1340478 | 9/2003 |
| GB | 1191633 | 5/1970 |
| GB | 1550-658 | 8/1979 |
| GB | 2244006 | 11/1991 |
| IT | 556381 | 11/1958 |
| RU | 2033772 | 4/1995 |
| SU | 560606 | 7/1977 |
| WO | WO03/003953 | 1/2003 |

* cited by examiner

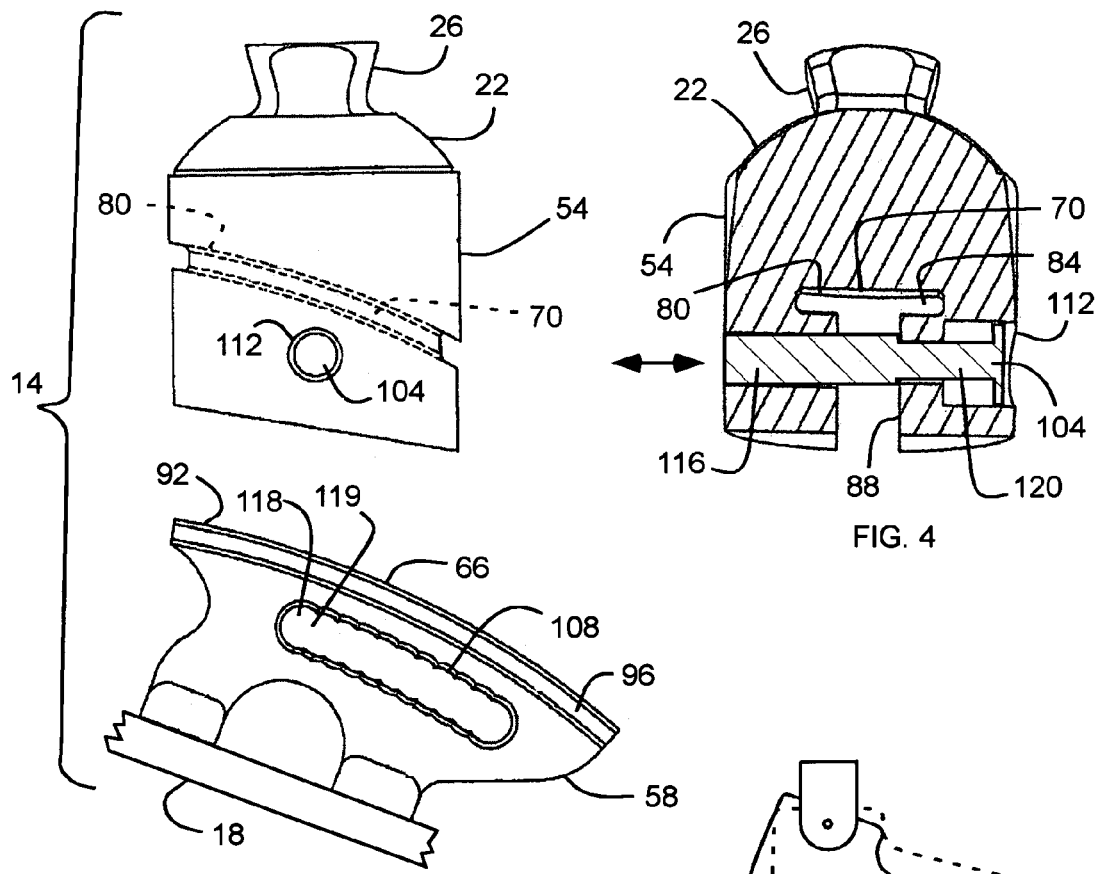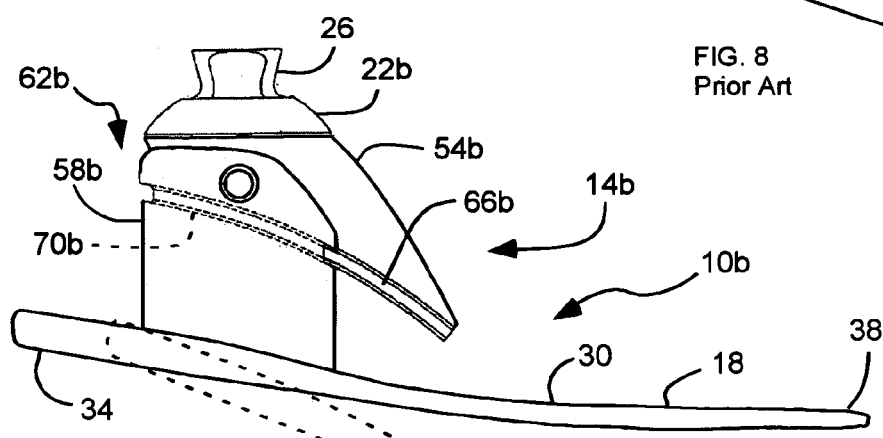

PROSTHETIC FOOT WITH AN ADJUSTABLE ANKLE AND METHOD

This is a continuation-in-part application of U.S. application Ser. No. 10/970,679, filed Oct. 20, 2004, now U.S. Pat. No. 7,462,201 which is a continuation-in-part of U.S. application Ser. No. 10/690,941, filed Oct. 21, 2003 now U.S. Pat. No. 6,966,933.

BACKGROUND OF THE INVENTION

1. Field of the Invention

The present invention relates generally to a prosthetic foot with an adjustable ankle. More particularly, the present invention relates to a prosthetic foot that simultaneously pivots downward and displaces forward.

2. Related Art

Many individuals have lost a limb for various reasons including war, accident, or disease. In most instances these individuals are not only able to live relatively normal lives, but physically active lives as well. Oftentimes, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element such as a spring. As the user steps onto the foot, the user's weight compresses the spring. As the user moves forward, the user's weight comes off the foot and the energy stored in the spring is used to propel the user forward.

Almost all of the past designs have focused on the major aspect of the prosthetic foot—movement of the ankle or foot as it relates to walking or running. Few designs consider the use of the foot with different shoes, such as different heel heights. For example, some shoes, such as sneakers, have a generally level or horizontally flat platform, while other shoes, such as high-heels or boots, have a heel that is relatively elevated with respect to the toe. It will be appreciated that the ankle of a natural foot pivots to accommodate different heels. In a natural foot, the foot and toes rotate to conform to the slope of the terrain. The artificial foot of previous designs usually incorporates a unitary foot that is incapable of such movement at the ankle.

Some artificial feet have a dynamic pivot or hinge at the ankle, or a dynamic ankle joint. See U.S. Pat. Nos. 4,442,554; 5,482,513 and 5,913,902. During use, a foot member often pivots or swings up and down about a pivot or axle.

Some artificial feet have an adjustable ankle with a swivel connection, or a foot that pivots at the ankle. For example, see U.S. Pat. Nos. 5,800,564 and 6,402,790. Such feet often have a foot member that selectively pivots about a pivot.

Other feet have a foot member that adjusts linearly back and forth. For example, see U.S. Pat. No. 6,228,124.

One problem with some of the above configurations is that they have proved unsatisfactory in use with different types of shoes, such as shoes with different heel heights. Another problem with some of the above configurations is that they are complicated or difficult to adjust.

SUMMARY OF THE INVENTION

It has been recognized that it would be advantageous to develop a prosthetic foot with an adjustable ankle. In addition it has been recognized that it would be advantageous to develop a prosthetic foot that provides a more natural feel or use when used with different shoes, such as shoes with different heel heights.

The invention provides an adjustable ankle device for a prosthetic foot. The adjustable ankle includes a lower portion adjustably coupled to an upper portion. The upper portion is coupled to a socket of an amputee. The lower portion is attached to a foot member that can have heel and toe sections. A movable coupling is disposed between the upper and lower portions. The movable coupling has a projection slidable in an arcuate slot oriented fore and aft, and defines an arcuate displacement path, such that the projection is constrained to slide fore and aft along the arcuate movement path.

In accordance with a more detailed aspect of the present invention, the adjustable ankle further comprises an actuator coupled to the movable coupling to move the upper and lower portions with respect to one another. A sensor is associated with the upper portion or the lower portion to sense frequency of contact, force of contact, or orientation of the upper portion or the lower portion, and to output a corresponding output signal. A controller is coupled to the actuator and the sensor to process the output signal of the sensor and engage the actuator in response to the output signal.

In accordance with a more detailed aspect of the present invention, the lower portion moves: 1) simultaneously in a downward and forward direction in which the lower portion simultaneously pivots downward and displaces forward with respect to the upper portion; and 2) simultaneously in a rearward and upward direction in which the lower portion simultaneously pivots upward and displaces rearward with respect to the upper portion. In addition, the lower portion is pivotal and displaceable with respect to the upper portion between at least two fixed positions, including: 1) a low position configured to dispose the heel section at a lower elevational position, and to dispose the heel section in a rearward position; and 2) a high position configured to dispose the heel section at a higher elevational position, and to dispose the heel section in a forward position.

In accordance with a more detailed aspect of the present invention, a tractor bolt can be rotatably disposed between the upper and lower portions, and driven by a motor. In addition, a level sensor can sense the orientation of the upper portion, and can send a signal to the motor to adjust the ankle automatically to level the foot or vertically orient the upper portion.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 3 is an exploded view of the adjustable ankle of FIG. 1;

FIG. 4 is a cross-sectional view of an upper portion of the adjustable ankle of FIG. 3;

FIG. 7 is a partial side view of another adjustable ankle in accordance with an embodiment of the present invention;

FIG. 8 is a side schematic view of a prosthetic foot with an adjustable ankle in accordance with the prior art;

DETAILED DESCRIPTION

Figure 1:
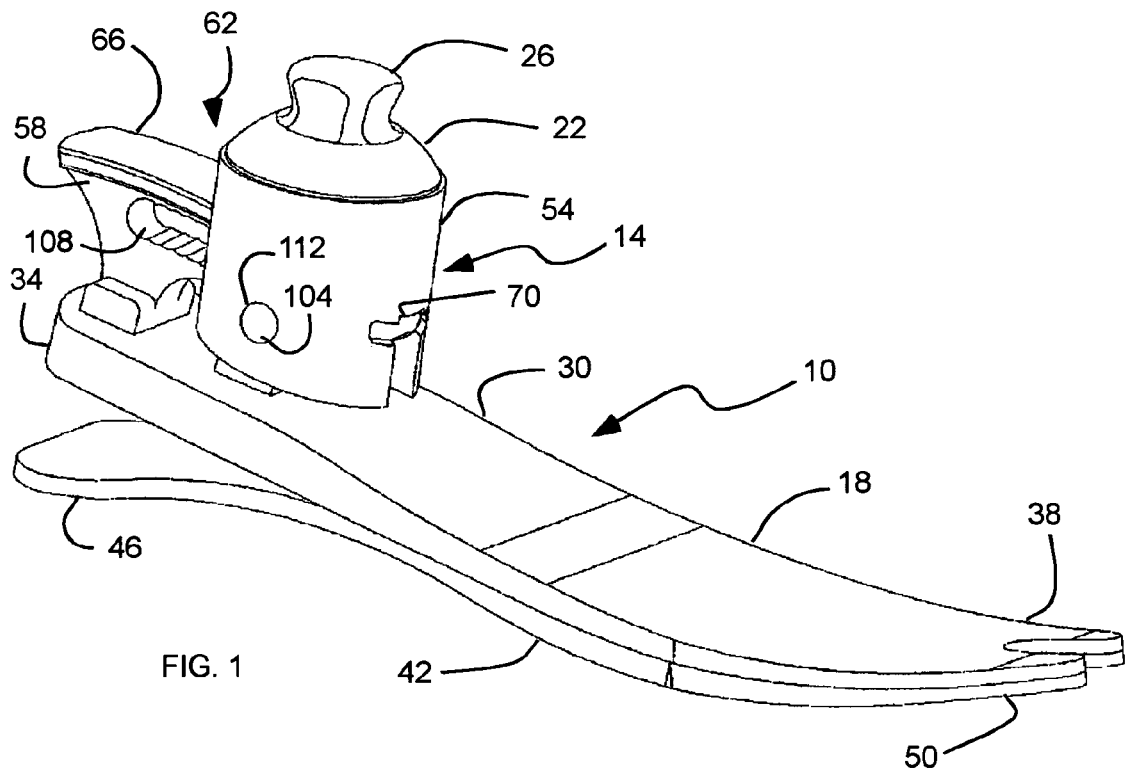
FIG. 1 is a perspective view of a prosthetic foot with an adjustable ankle in accordance with an embodiment of the present invention.
Figure 5:
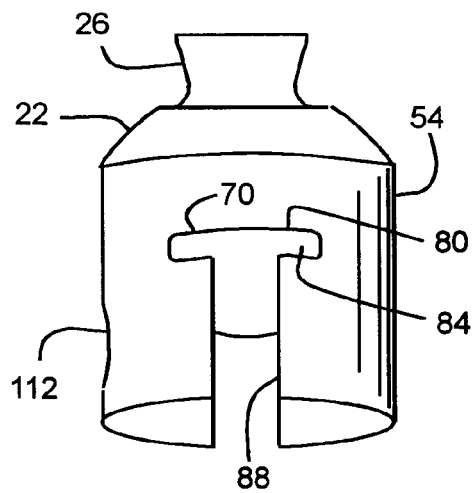
FIG. 5 is a front view of the upper portion of the adjustable ankle of FIG. 3.
Figure 6:
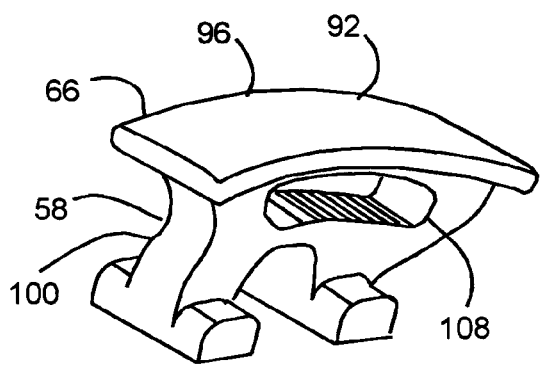
FIG. 6 is a perspective view of a lower portion of the adjustable ankle of FIG. 3.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIGS. 1-6, a prosthetic foot, indicated generally at 10, with an adjustable ankle, indicated generally at 14, in accordance with the present invention is shown for adjusting the prosthetic foot. The adjustable ankle 14 can adjust the angle of the foot 10, and the elevation of the heel. The adjustable ankle 14 can be utilized to quickly and easily adjust the foot 10 for use with different shoes, such as shoes with different heel heights. As described in greater detail below, the prosthetic foot 10 and adjustable ankle 14 allow the prosthetic foot to adjust by simultaneously pivoting downward and displacing forward. Thus, as a toe section pivots downward to accommodate a higher heel, the foot or heel also displaces forwardly. Surprisingly, it has been found that such a configuration provides a more natural feel.

The prosthetic foot 10 can have various different configurations. For example, the foot 10 can include one or more foot members 18 adjustably attached to an attachment member 22 by the adjustable ankle 14. Thus, the adjustable ankle 14 can be coupled between the attachment member 22 and the foot members 18. The attachment member 22 can be operatively coupled to a socket that receives an amputee's stump, as is known in the art. For example, the attachment member can include an inverted frustopyramidal boss 26 that can be received in a corresponding cavity (not shown), as is known in the art. Such inverted frustopyramidal type connections are typically used to selectively connect a prosthetic foot to the socket in a desired orientation, and can be used to adjust the angle between the foot and the socket. The boss 26 is held within a socket by a plurality of set screws, and is thus difficult to quickly adjust.

The foot members 18 can have various different members with various different configurations. For example, the foot members 18 can include a forefoot 30 that extends between a heel section 34 at a rear of the foot and a toe section 38 at a toe location of a natural foot. In addition, the foot members 18 can include a footplate 42 extending substantially the length of the foot between a heel section 46 at a heel location of a natural foot and a toe section 50 at the toe location. The toe section 50 of the footplate 42 can be attached to the toe section 38 of the forefoot 30. The foot members 30 and 42 can be flexible and resilient energy storing members that act as springs to bend or flex during use. The foot members 30 and 42 can include a composite material, such as a carbon or graphite fiber in an epoxy matrix.

The adjustable ankle 14 can include upper and lower portions 54 and 58 adjustably coupled to one another. The upper portion 54 can be coupled to the socket or attachment member 22. The upper portion 54 and attachment member 22 can be integrally formed, and the upper portion 54 can form part of the attachment member 22. The lower portion 58 can be coupled to the foot member 18 or forefoot 30.

A movable coupling is disposed between the upper and lower portions. The movable coupling allows the lower portion to move: 1) simultaneously in a downward and forward direction in which the lower portion simultaneously pivots downward and displaces forward with respect to the upper portion; and 2) simultaneously in a rearward and upward direction in which the lower portion simultaneously pivots upward and displaces rearward with respect to the upper portion. In addition, the lower portion is pivotal and displaceable with respect to the upper portion between at least two fixed positions, including: 1) a low position (FIG. 2a) configured to dispose the heel section at a lower elevational position, and to dispose the prosthetic foot or heel section in a rearward position; and 2) a high position (FIG. 2b) configured to dispose the heel section at a higher elevational position, and to dispose the prosthetic foot or heel section in a forward position.

The coupling can be oriented upright with respect to the lower portion 58, with one end of the coupling being disposed at a lower elevation with respect to a central section of the coupling. The movable coupling can include a displacement member slidable in a displacement track disposed between the upper and lower portions. The lower portion is movable from a rearward position to a forward and downward position, with the toe section pivoted downwardly and the heel section displaced forwardly. The movable coupling can include an arched coupling 62 formed or disposed between the upper and lower portions 54 and 58. The arched coupling 62 forms an arc that is oriented upright, with at least one end of the arched coupling or arc being disposed at a lower elevation with respect to a central section of the arched coupling. The arched coupling 62 includes an arcuate projection 66 slidable in an arcuate slot 70. The arcuate projection 66 can be or can form at least a portion of the lower portion 58, and thus can extend from the foot member 18 or forefoot 30. The arcuate slot 70 can be formed in the upper portion 54 or the attachment member 22. The arcuate projection 66 and arcuate slot 70 also have an upright orientation, as described above.

The arched coupling 62 (and the arcuate projection and slot 66 and 70) allows the arcuate projection 66 (and the lower portion 58 and foot portion 18) to both 1) pivot downward and 2) displace forward. Thus, the toe section 38 pivots downward and the heel section 34 simultaneously displaces forward (indicated by arrow 74 in FIG. 2b) with respect to the attachment member 22. Similarly, the arcuate projection 66 can both 1) pivot upward and 2) displace rearward. Thus, the toe section 38 pivots upward and the heel section 34 simultaneously displaces rearward (indicated by arrow 78 in FIG. 2a) with respect to the attachment member.

Figure 2A:
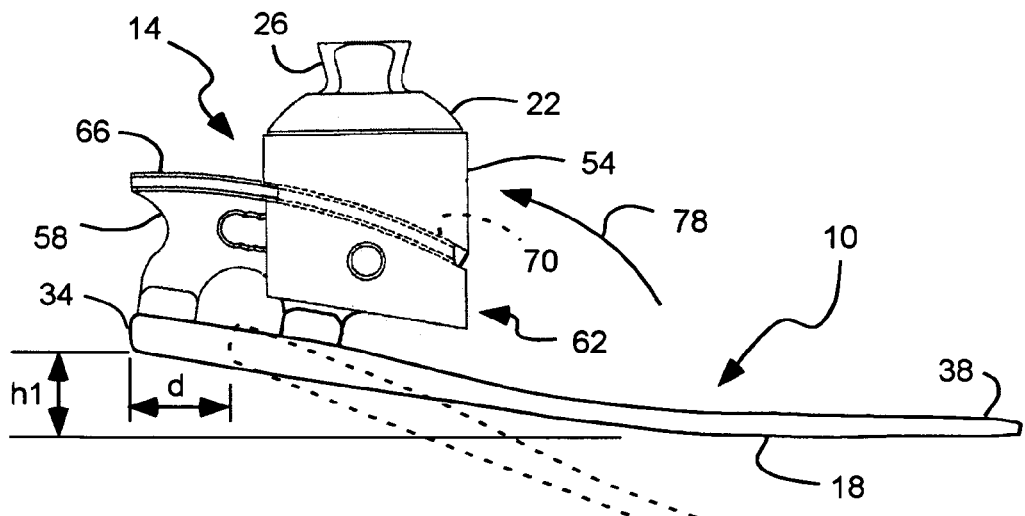
FIG. 2a is a side view of the prosthetic foot with an adjustable ankle of FIG. 1, shown in a first, lower position.
Figure 2B:
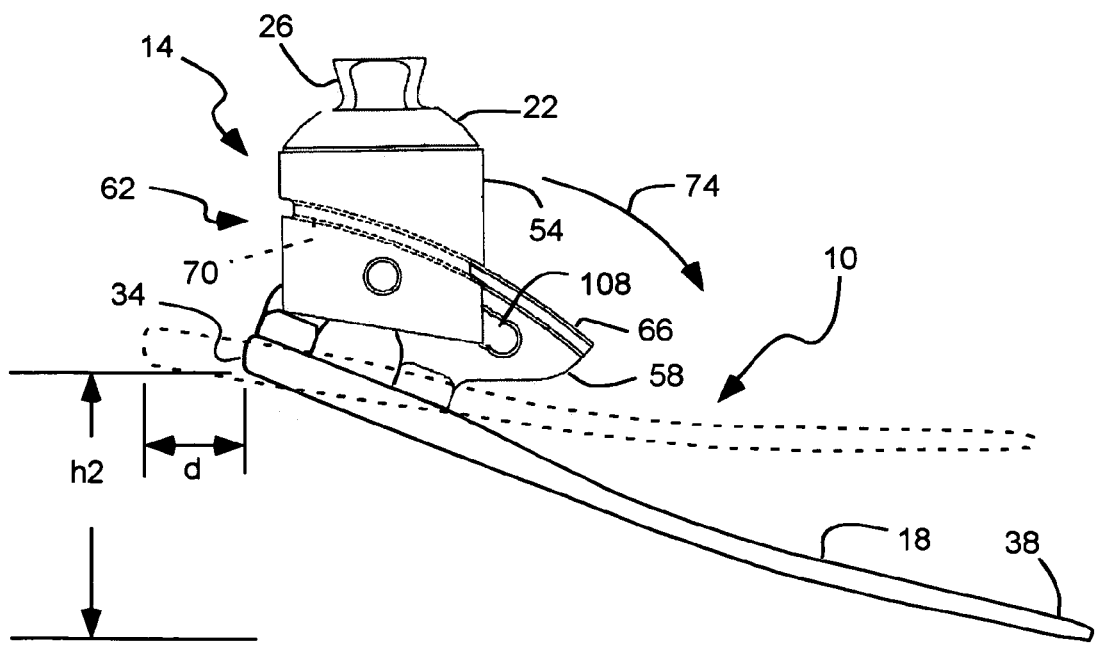
FIG. 2b is a side view of the prosthetic foot with an adjustable ankle of FIG. 1, shown in a second, higher position.

The foot member 18 is pivotal and displaceable between at least two positions, including 1) a low position and 2) a high position, as shown in FIGS. 2a and 2b. In the low position (FIG. 2a), the toe section 38 of the foot member 18 is pivoted in an upward direction 78 with respect to the arched coupling 62 (or attachment section 22). Thus, the heel section 34 (of attachment section 22) is disposed at a relatively lower elevational position h1 with respect to the high position (FIG. 2b). The low position can be used with flatter shoes, such as sneakers, flats, loafers and the like. In addition, the foot member 18 or heel section 34 is disposed in a rearward position, indicated by solid lines in FIG. 2a. In the low position, the forefoot 18 not only pivots upward, but displaces rearward so that the heel section 34, represented by d.

In the high position (FIG. 2b), the toe section 38 of the foot member 18 is pivoted in a downward direction 74 with respect to the arched coupling 62 (or attachment section 22). Thus, the heel section 34 (or attachment section 22) is disposed at a higher elevational position h2 with respect to the low position (FIG. 2a). Thus, the high position can be used with more elevated shoes, such as high heels, cowboy boots and the like. In addition, the foot member 18 or heel section 34 is disposed in a forward position, shown in solid lines, indicated by solid lines in FIG. 2b, as opposed to a rearward position. In the high position, the foot member 18 not only pivots downward, but displaces forward so that the heel section 34 is in a forward position, represented by d. Surprisingly, it has been found that as the elevation of the attachment section 22 is increased, a more forward position of the foot member 18 or heel section 34 provides a more natural feel. It will be appreciated that a simple pivot adjustment causes the foot to move rearward as it pivots downward, as shown in FIG. 8.

As stated above, the arcuate slot 70 can be formed in the attachment section 22 or upper portion 54 of the arched coupling 62. The arcuate slot 70 can have an upper wall 80 that is arcuate or curved. In addition, the arcuate slot 70 can include an enlarged cavity 84 and a narrower gap 88. The enlarged cavity 84 is arcuate or curved. The narrower gap 88 can extend from a bottom of the upper portion 54 to the enlarged cavity 84. The arcuate slot 70 can have a T-shaped cross-section, with the enlarged cavity forming the upper horizontal portion of the T-shape, and the narrower gap 88 forming the lower vertical portion of the T-shape. In addition, the enlarged cavity 84 and narrower gap can extend entirely through the upper portion 54, or from the front to the back. As described above, the arc or curvature of the arcuate slot 70 and enlarged cavity 84 is oriented upright, or has at least one end that extends downward. In addition, the arc or curvature can be oriented to slope or angle downward towards the toe section 38.

The arcuate projection 66 can be formed on the lower portion 58 of the arched coupling 62, and can extend from the foot member 18. The arcuate projection 66 can have an upper wall 92 that is acruate or curved, with an arcuate or curved bearing surface that bears against the upper wall 80 of the arcuate slot 70 during use. The arcuate projection 66 can include an enlarged head or flange 96 and a narrower web 100. The enlarged head 96 is arcuate or curved. The narrower web 100 can extend from the bottom of the lower portion 58, or the foot member 18, to the enlarged head 96. The arcuate projection 66 can have a T-shaped cross-section with the enlarged head 96 forming the upper horizontal portion of the T-shape, and the narrower web 100 forming the lower vertical portion of the T-shape. The arcuate projection 66 and arucate slot 70 can be sized so that projection 66 can slide in the slot 70 with relatively little play. As described above, the arc or curvature of the arcuate projection 66 and enlarged head 96 is oriented upright. Thus, the arc or curvature of the arcuate projection 66 and enlarged head 96 (or bearing surface) can be convex, and can face upward and forward.

The adjustable ankle 14 with the arcuate projection 66 slidable in the arcuate slot 70 is one example of a means for movably coupling the lower portion 58 to the upper portion 54, or for movably coupling the foot member 18 with respect to the attachment member 22. In addition, the means for movably coupling can also be means for simultaneously 1) pivoting the lower portion 58, foot member 18 and/or toe section 38 downward with respect to the upper portion 54 or attachment member 22, and 2) displacing the lower portion 58, foot member 18 and/or heel section 34 forward with respect to the upper portion 54 or attachment member 22. Furthermore, the means for movably coupling can further be means for simultaneously 1) pivoting the toe section 38 of the foot member 18 downward with respect to the heel section 34, and 2) displacing the foot member 18 or heel section 34 forward with respect to the upper portion 54.

In addition, the adjustable ankle 14 with the arcuate projection 66 slidable in the arcuate slot 70 is one example of a means for selectively adjusting the elevational position of the heel section 34 with respect to the toe section 38 between at least two fixed positions, including 1) a low position (FIG. 2a) in which the heel section 34 is disposed at a lower elevational position with respect to the toe section 38, and in which the foot member 18 or heel section 34 is disposed in a rearward position with respect to the upper portion 54; and 2) a high position (FIG. 2b) in which the heel section 34 is disposed at a higher elevational position with respect to the toe section 38, and in which the foot member 18 or heel section 34 is disposed in a forward position with respect to the upper portion 54.

The adjustable ankle 14, and the arcuate projection 66 and arcuate slot 70, can have different configurations, including a dovetail-type connection. In addition, the heel section also can move up and down as the foot member pivots.

The adjustable ankle 14 also can include a locking mechanism that can be quickly operated to adjust the prosthetic foot 10. The locking mechanism can include a locking pin 104 and an elongated aperture 108. The aperture 108 can be formed in the lower portion 58, and the pin 104 can be disposed in a bore 112 on the upper portion 54. The aperture 108 can be formed by a plurality of overlapping bores so that a plurality of ridges are formed in the aperture to separate the aperture into discrete sections 118 interconnected by a channel 119. Thus, the pin can be disposed at a plurality of discrete positions. The pin 104 can include an enlarged portion 116 with a greater diameter for filling a discrete section and locking the arcuate projection 66 in the arcuate slot 70. The pin 104 can be displaced so that the enlarged portion 116 is displaced out of the discrete section and replaced by a smaller portion 120 with a smaller diameter that travels in the channel allowing the arcuate projection 66 to slide in the arcuate slot 70.

A method for adjusting a prosthetic foot, or using the prosthetic foot described above, includes pivoting a toe section 38 of a foot member 18 in a downward direction with respect to an attachment member 22 so that a heel section 34 of the foot member is disposed at a higher elevational position h2. In addition, the foot member 18 or heel section 34 is simultaneously displaced in a forward direction with respect to the attachment member 22 so that the heel section 34 is disposed at a greater forward position L2.

The above prosthetic foot 10, adjustable ankle 14, and arched coupling 62 have been described as having the arcuate slot 70 formed in the upper portion 54 or attachment section 22, and the arcuate projection 66 as part of the lower portion 58 or extending from the foot portion 18. This configuration can be reversed. Referring to FIG. 7, another prosthetic foot 10b is shown which is similar in many respects to that shown above, but with an arcuate projection 66b as part of the upper portion 54b, and an arcuate slot 70b formed in the lower portion 58b.

As described above, the attachment section 22 and upper portion 58 of the coupling 62 can be a single piece.

Figure 9:
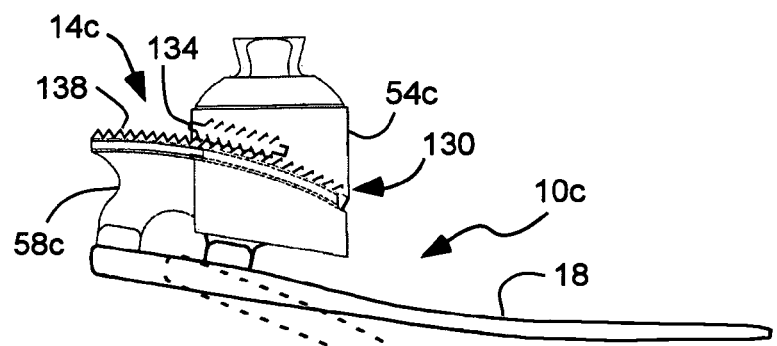
FIG. 9 is a side view of another adjustable ankle in accordance with an embodiment of the present invention.

Referring to FIG. 9, a prosthetic foot 10c is shown with an adjustable ankle 14c that is similar in some aspects to those described above. In addition, the adjustable ankle 14c can utilize a worm gear 130 to selectively adjust the elevational height of the ankle. The worm gear 130 can include a drive screw 134 on the upper portion 54c that engages screw threads 138 on the lower portion 58c. The drive screw 134 can be rotated, causing the lower portion 58c to both pivot and displace. The adjustable ankle 14c and/or worm gear 130 is another example of a means for movably coupling the lower portion 58c to the upper portion 54c, or for movably coupling the foot member 18c with respect to the attachment member. In addition, the means for movably coupling can also be means for simultaneously pivoting and displacing, as described above. In addition, the adjustable ankle 14c and worm gear 130 can form at least part of a means for selectively adjusting the elevational position of the heel section with respect to the toe section between at least two fixed positions, as discussed above.

Figure 10:
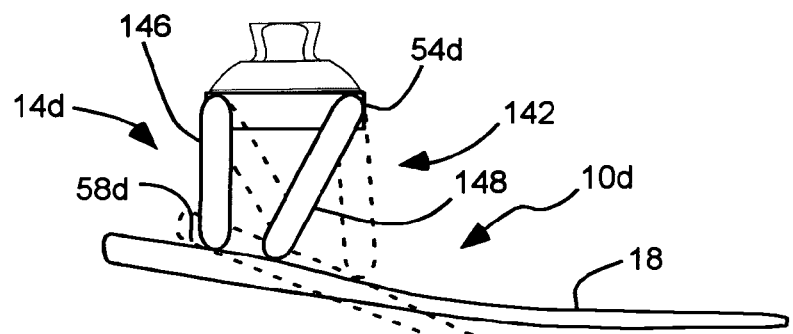
FIG. 10 is a side view of another adjustable ankle in accordance with an embodiment of the present invention.

Referring to FIG. 10, a prosthetic foot 10d is shown with an adjustable ankle 14d that is similar in some aspects to those described above. In addition, the adjustable ankle 14d can include a four bar linkage 142 to selectively adjust the elevational height of the ankle. The upper portion 54d or attachment member can form one of the links. Similarly, the lower portion 58d or foot member 18 can form another link. Another pair of links 146 and 148 can extend between the upper portion 54d and lower portion 58d or foot member 18. The links 146 and 148 can have different lengths, and/or have their ends attached at different lengths, in order to obtain the pivotal motion and displacement. The adjustable ankle 14d and/or four bar linkage 142 is another example of a means for movably coupling the lower portion 58d to the upper portion 54d, or for movably coupling the foot member 18d with respect to the attachment member. In addition, the means for movably coupling can also be means for simultaneously pivoting and displacing, as described above. In addition, the adjustable ankle 14d and four bar linkage 142 can form at least part of a means for selectively adjusting the elevational position of the heel section with respect to the toe section between at least two fixed positions, as discussed above.

Figure 11:
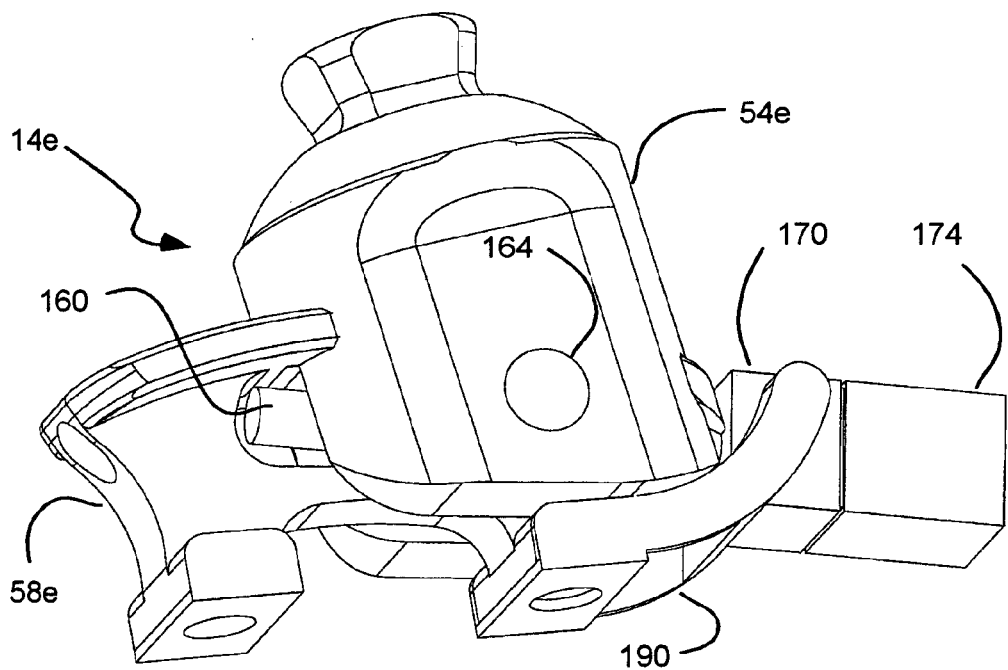
FIG. 11 is a perspective view of another adjustable ankle in accordance with an embodiment of the present invention.
Figure 12:
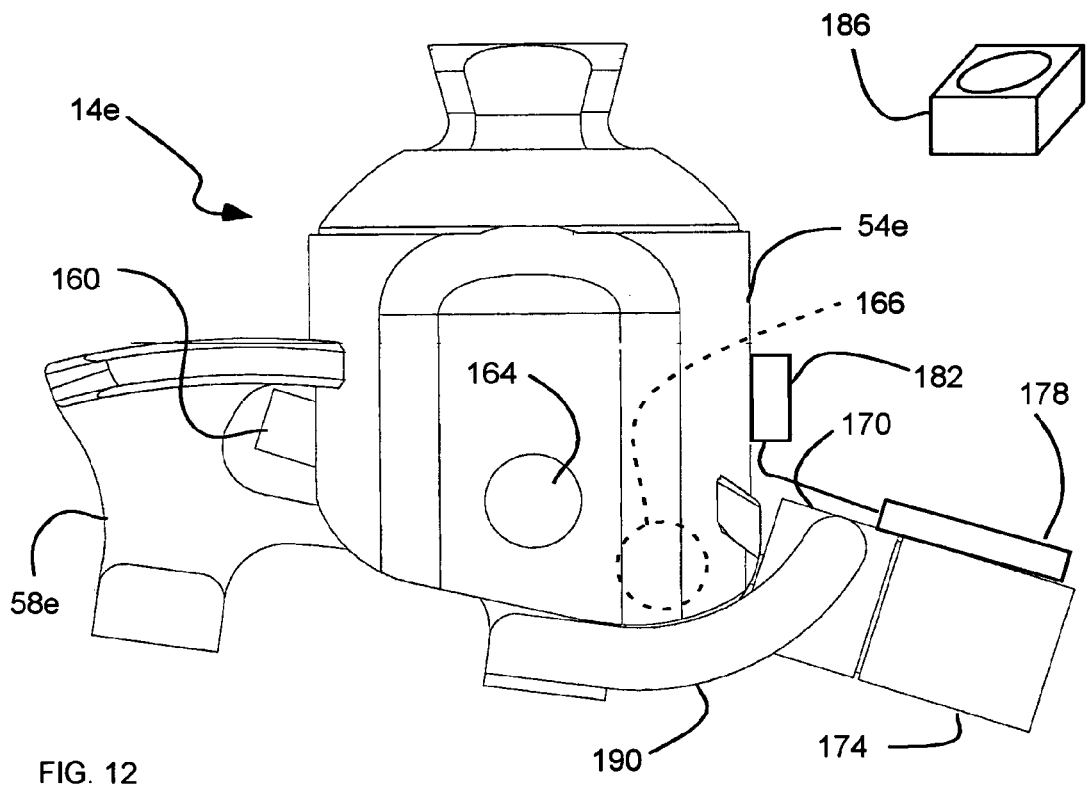
FIG. 12 is a side view of the adjustable ankle of FIG. 11.

Referring to FIGS. 11 and 12, an adjustable ankle 14e of a prosthetic foot is shown that is similar in many respects to those described above. The adjustable ankle 14e can be autoleveling, and/or can include motorized adjustment. Thus, the ankle can sense the orientation of socket based on the type of shoe that is worn, and adjust the ankle accordingly. In addition, the ankle can be remotely adjusted, or can have powered adjustment.

The ankle 14e can include upper and lower portions 54e and 58e adjustably coupled to one another, similar to those described above. The lower portion 58e can be, or can include, a slide coupled to a foot member or forefoot. The upper portion 54e can be a slide connector that slidably engages the slide, and can be coupled to a socket or attachment member. (The socket and foot member or forefoot are not shown for clarity, but may be similar to those described above.)

In addition, the ankle 14e includes a motor-driven tractor bolt 160 rotatably coupled to or carried by the slide or lower portion 58e, for example in a cavity or opening of the slide. The tractor bolt 160 can be a threaded rod, or has screw threads. A connector spool 164 can be coupled to or carried by the connector slide or upper portion 54e. The connector spool 164 is threaded and engages the threads of the tractor bolt 160. Thus, as the tractor bolt 160 rotates, the connector spool 164, and thus the connector slide or upper portion 54e, is displaced along the slide or lower portion 58e, adjusting the angle of the foot, and the elevation of the heel.

A fore spool 166 can be carried by the lower portion 58e. The tractor bolt 160 can pass through the fore spool 166 so that the fore spool secures the tractor bolt while allowing the tractor bolt to turn.

A motor 170 can be carried by the lower portion 58e, and operatively coupled to the tractor bolt 160 to turn or rotate the tractor bolt. The motor 170 can be a DC motor driven by a power source 174, such as a battery. A controller or control electronics 178 can be operatively coupled to the power source and motor to provide a control signal or drive signal to selectively turn the tractor bolt to achieve the desired relative position between the upper and lower portions, and thus the angle of the foot and elevation of the heel. The control electronics can include a processor or the like. One or more sensors 182 can be coupled to, or carried by, the upper portion 54e to sense an orientation of the upper portion. The sensor 182 can be coupled to the control electronics 178 and can provide a level signal that is processed by the control electronics. Thus, the ankle 14e can be self adjusting to obtain a vertical orientation of the upper portion. Alternatively, one or more sensors can be coupled to the socket, foot, etc.

In addition, the control electronics 178 can include means for inputting control signals and/or commands to operate the motor and adjust the ankle. For example, a remote control or "key-bob" 186 with a transmitter to send a signal to a receiver associated with the control electronics. The remote control 186 can include one or more buttons to adjust the ankle up or down. Alternatively, the control electronics can include one or more buttons to adjust the ankle. Furthermore, the input means can include any type of electrical connection, such as input from another computer, PDA, etc. These are examples of means for a user to manually control the motor, as to automatic control by a sensor.

The motor 170 can be coupled to or mounted to the lower portion 58e by a motor clip or mount 190. The mount 190 can be coupled to and between the lower portion 58e and the motor 170. The mount 190 can be coupled to the lower portion 58e between the lower portion and the foot or foot member, and can extend forwardly to a front of the ankle. The motor can be disposed at a front of the ankle as shown.

It is of course understood that the adjustable ankle described above can have various different configurations. For example, the tractor bolt can remain stationary or non-rotatable, while the connector spool or another threaded nut can be rotatably coupled to the slide connector or upper portion and rotated by the motor. As another example, the tractor bolt can be carried by the slide connector or upper portion and the connector spool can be carried by the slide or lower member.

Figure 13:
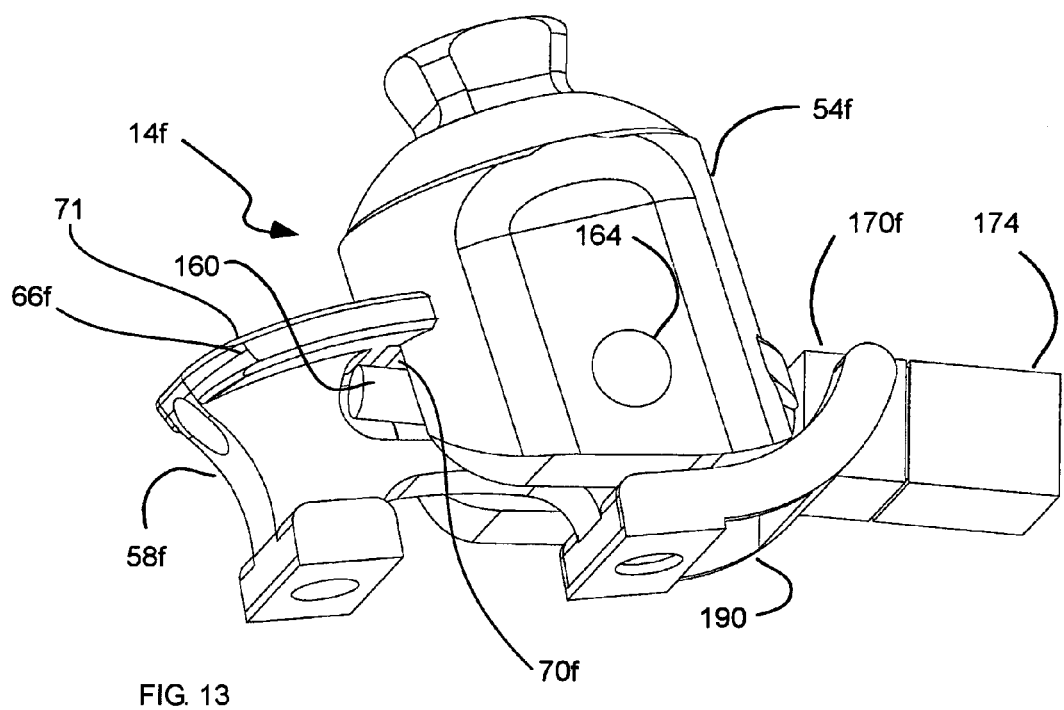
FIG. 13 is a perspective view of another adjustable ankle in accordance with an embodiment of the present invention.
Figure 14:
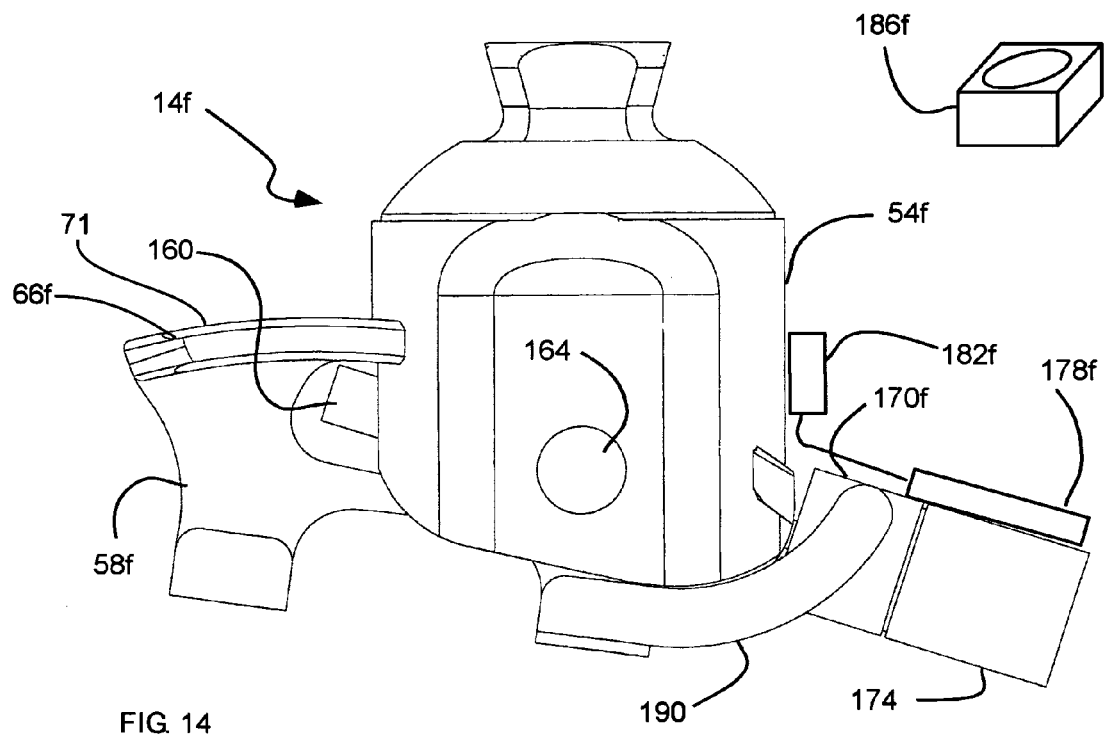
FIG. 14 is a side view of the adjustable ankle of FIG. 13.

Referring to FIGS. 13-14, an adjustable ankle 14*f* of a prosthetic foot is shown that is similar in many respects to those described above. The adjustable ankle 14*f* can be auto-leveling, and/or can include sensing and motorized adjustment. Thus, the ankle can sense the orientation of the terrain the prosthetic foot is contacting, and adjust the ankle accordingly. In addition, the ankle can be remotely adjusted, or can have powered adjustment.

The adjustable ankle 14*f* can have an attachment portion or an upper portion 54*f* that can be coupled to a socket of an amputee. A foot portion or a lower portion 58*f* can be adjustably coupled to the upper portion 54*f* and can be attached to a foot member (not shown). A movable coupling can be disposed between the upper portion and the lower portion. The movable coupling can have a projection 66*f* slidable in an arcuate slot 70*f* that is oriented fore and aft relative to a toe and heel of an attached foot member.

The arcuate slot 70*f* can have a T-shaped cross-sectional shape, and the arcuate projection 66*f* can have a T-shaped cross-sectional shape that corresponds to the T-shaped cross-sectional shape of the arcuate slot 70*f*. Thus, the projection 66*f* can fit into, and slide within, the arcuate slot 70*f*. Additionally, the projection 66*f* can be an arcuate projection, and can include a convex bearing surface 71.

The projection 66*f* and arcuate slot 70*f* can define an arcuate displacement path, such that the projection 66*f* is constrained to slide fore and aft along the arcuate movement path. Additionally, the lower portion 58*f* can be constrained to fore and aft arcuate displacement with respect to the upper portion 54*f* between at least two fixed positions, namely a low position and a high position. In the low position the heel section is disposed at a lower elevational position, and the heel section is disposed in a rearward position. In the high position, the heel section is disposed at a higher elevational position, and the heel section is disposed in a forward position. Thus, when the lower portion 58*f* is in an upward and rearward position, movement of the lower portion 58*f* is restricted to simultaneous movement in a downward and forward direction in which the lower portion 58*f* simultaneously pivots downward and displaces forward relative to the upper portion 54*f*. Additionally, when the lower portion 58*f* is in a downward and forward position, movement of the lower portion 58*f* is restricted to simultaneous movement in a rearward and upward direction in which the lower portion 58*f* simultaneously pivots upward and displaces rearward relative to the upper portion 54*f*.

The adjustable ankle 14*f* can also have an actuator 170*f* that is coupled to the movable coupling, and moves the upper portion 54*f* and the lower portion 58*f* with respect to one another. A sensor 182*f* can be associated with the upper portion 54*f* or the lower portion 58*f* as shown by dashed lines at 184. Alternatively, the sensors 182*f* or 184*f* can be associated with the socket or the foot. Additionally, the adjustable ankle 14*f* can have a sensor 182*f* on the upper portion 54*f* and a sensor 184 on the lower portion 58*f*. The sensors 182*f* and 184 can sense frequency of contact, force of contact, or orientation of the upper portion 58*f* and/or the lower portion 54*f*. The sensors 182*f* and 184 can output a corresponding output signal relative to the frequency of contact, force of contact, or orientation of the upper portion 54*f* and/or the lower portion 58*f*.

A controller 178*f* can be operatively coupled to the actuator 170*f* and the sensors 182*f* and 184. The controller 178*f* can process the output signal of the sensors 182*f* and 184 and engage the actuator 170*f* in response to the output signal. The controller 178*f* can automatically drive the actuator 170*f* to move the lower portion 58*f* to a predetermined initial position in response to a predetermined signal from the sensors 182*f* and 184. In this way the controller 178*f* can automatically level the lower portion 58*f* and an attached prosthetic foot with respect to the upper portion 54*f* or terrain. In addition, the sensor 182*f* can sense the orientation of the upper portion 54*f* and send a signal to the actuator to move the lower portion 58*f* so that the upper portion is in a desired orientation, such as vertical.

The controller 178*f* can operate in several modes in order to support different activities by the user. For example, the controller 178*f* can have a walk, a run mode, a downhill mode, an uphill mode, and a level mode. In the downhill mode, the controller can respond to a relatively lower frequency and force of impact on the lower portion, as determined by the sensors 182*f* and 184. In the run mode, the controller can respond to a relatively higher frequency and force of impact on the lower portion as determined by the sensors 182*f* and 184. In the downhill mode, the controller can move the lower portion to a forward and downward position corresponding to walking downhill. In the uphill mode, the controller can move the lower portion to a rearward and upward position corresponding to walking up hill. In the level mode, the controller can move the lower portion to a relatively level position for walking on relatively level terrain.

A user input interface 186*f*, such as the "key-bob" 186 described above, or a remote programming device as shown in FIG. 14, can allow a user to program the controller 178*f* to adjust the lower portion 58*f* to a position corresponding to changes in slope. In this way, the user can actively change the position of the lower portion 58*f* to actual terrain changes encountered during use of the adjustable ankle 14*f*. Additionally, the user can program the foot to anticipated or known changes that will be encountered during use of the adjustable ankle. In this way the ankle will automatically adjust to changes in terrain during use.

The user input interface 186*f* is an example of means for automatically controlling the actuator 170*f*. The actuator 170*f* can also have means for manually controlling the actuator. For example, the actuator 170*f* can be controlled manually through input switches located directly on the controller 178*f*, or a manual drive mechanism such as a drive screw of worm gear can coupled to the actuator 170*f* to manually adjust the position of the lower portion 58*f*.

Figure 15:
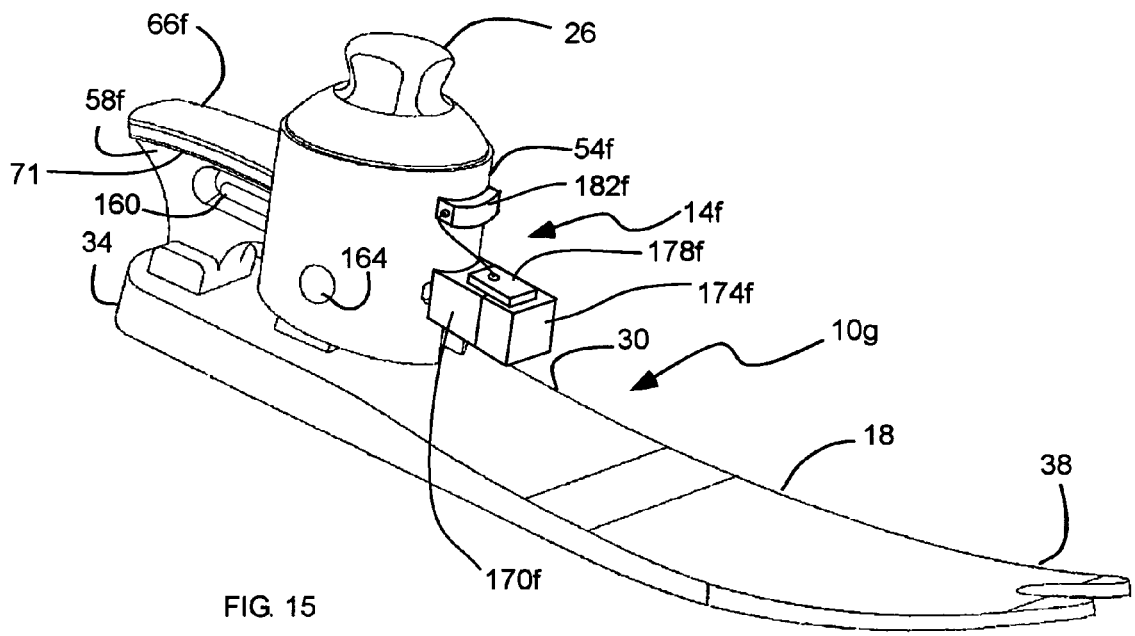
FIG. 15 is a perspective view of another prosthetic foot with the adjustable ankle of FIG. 13 in accordance with an embodiment of the present invention.
Figure 16:
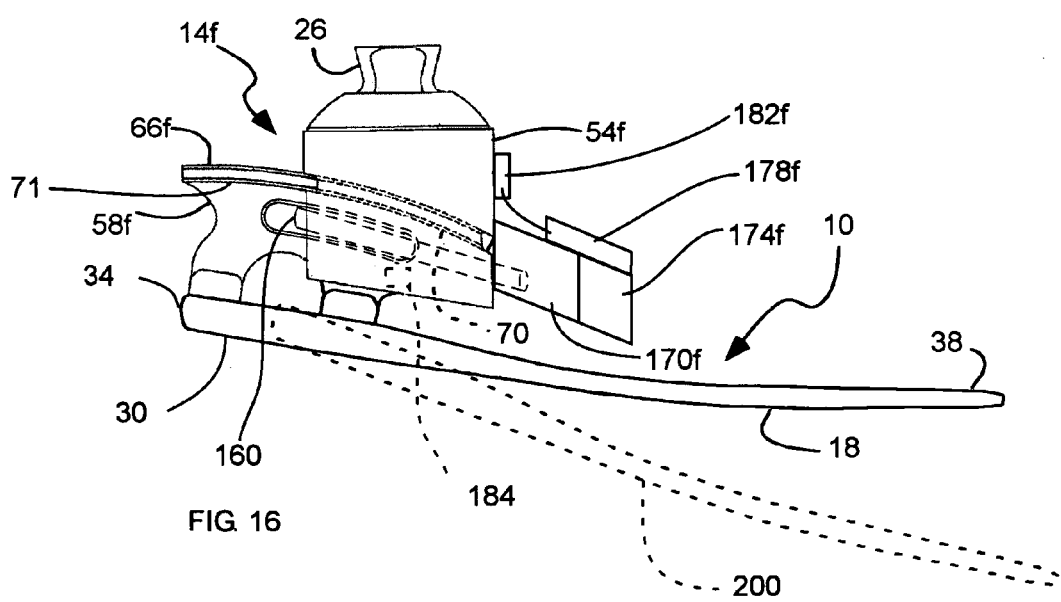
FIG. 16 is a side view of the prosthetic foot of FIG. 15.

Referring to FIGS. 15 and 16, a prosthetic foot, indicated generally at 10, that is similar in many respects to those described above is shown with the adjustable ankle 14*f* shown in FIGS. 12 and 13. The prosthetic foot device 10 can have an attachment member 26 that can be coupled to a socket of an amputee. A foot member 30 can be adjustably coupled to the attachment member 26 and can have heel 34 and toe sections 48. The adjustable ankle 14*f* can couple the foot member 30 to the attachment member 26.

FIG. 16 also illustrates the low and high positions of the lower portion 58*f* with respect to the upper portion 54*f*. Specifically, as described above, the lower portion 58*f* can be constrained to fore and aft arcuate displacement with respect to the upper portion 54*f* between at least two fixed positions, namely a low position and a high position. In the low position, the heel section 34 is disposed at a lower elevational position, and the heel section 34 is disposed in a rearward position. In the high position, as illustrated by dashed lines at 200, the heel section 34 is disposed at a higher elevational position, and the heel section 34 is disposed in a forward position.

The present invention also provides for a method for adjusting a prosthetic foot including sensing the frequency of contact, the force of contact, or the orientation of a lower portion or an upper portion of a foot member with a sensor that outputs a corresponding signal. The output signal from the sensor system can be processed with a controller to determine a position for the lower portion with respect to the upper portion. An actuator can be actuated to move the lower portion of the foot member to the position determined. Movement of the lower portion can be constrained with respect to the upper potion to an arcuate displacement path oriented fore and aft with an arcuate projection slidable in an arcuate slot so that when the lower portion is in an upward and rearward position, movement of the lower portion is restricted to simultaneous movement in a downward and forward direction in which the lower portion simultaneously pivots downward and displaces forward relative to the upper portion. Additionally, when the lower portion is in a downward and forward position, movement of the lower portion is restricted to simultaneous movement in a rearward and upward direction in which the lower portion simultaneously pivots upward and displaces rearward relative to the upper portion.

It is to be understood that the above-referenced arrangements are only illustrative of the application for the principles of the present invention. Numerous modifications and alternative arrangements can be devised without departing from the spirit and scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed is:

1. An adjustable ankle device for a prosthetic foot, comprising:
    a) an upper portion configured to be coupled to a socket of an amputee;
    b) a lower portion, adjustably coupled to the upper portion, configured to be attached to a foot member;
    c) a movable coupling, disposed between the upper and lower portions, having an arcuate projection slidable in an arcuate slot oriented fore and aft with the arcuate projection having a shape corresponding to the arcuate slot, and defining an arcuate displacement path, such that the projection is constrained to slide fore and aft along the arcuate movement path, to restrict movement to:
        i) simultaneously in a downward and forward direction in which the lower portion simultaneously pivots downward and displaces forward relative to the upper portion; and
        ii) simultaneously in a rearward and upward direction in which the lower portion simultaneously pivots upward and displaces rearward relative to the upper portion;
    d) an actuator, coupled to the movable coupling, to move the upper and lower portions with respect to one another;
    e) a sensor, associated with the upper or lower portions, to sense frequency of contact, force of contact, or orientation of the upper portion or the lower portion, and to output a corresponding output signal; and
    f) a controller, coupled to the actuator and the sensor, to process the output signal of the sensor and engage the actuator in response to the output signal.

2. A device in accordance with claim 1, wherein the controller automatically drives the actuator to move the lower portion to a predetermined initial position in response to a predetermined signal from the sensor.

3. A device in accordance with claim 1, wherein the controller further comprises:
    a user input interface, configured to allow a user to program the controller to adjust the lower portion to a position corresponding to changes in slope.

4. A device in accordance with claim 1, wherein the controller has a walk mode to respond to a relatively lower frequency and force of impact on the lower portion, and a run mode to respond to a relatively higher frequency and force of impact on the lower portion.

5. A device in accordance with claim 1, wherein the controller has:
    i) a downhill mode to move the lower portion to a forward and downward position corresponding to walking downhill;
    ii) an uphill mode to move the lower portion to a rearward and upward position corresponding to walking up hill; and
    iii) a level mode to move the lower portion to a relatively level position for walking on relatively level terrain.

6. A device in accordance with claim 1, further comprising: means for a user to manually control the actuator.

7. A device in accordance with claim 1, wherein the lower portion is constrained to fore and aft arcuate displacement with respect to the upper portion between at least two fixed positions, including:
    a) a low position, in which the heel section is disposed at a lower elevational position, and in which the heel section is disposed in a rearward position; and
    b) a high position, in which the heel section is disposed at a higher elevational position, and in which the heel section is disposed in a forward position.

8. A device in accordance with claim 1, wherein the arcuate slot has a T-shaped cross-sectional shape; and wherein the arcuate projection has a T-shaped cross-sectional shape.

9. A device in accordance with claim 1, wherein the arcuate slot includes an enlarged cavity and wherein the arcuate projection includes an enlarged head.

10. A prosthetic foot device with an adjustable ankle, comprising:
    a) an attachment member configured to be coupled to a socket of an amputee;
    b) a foot member, coupled to and adjustable with respect to the attachment member with an enlarged head of an arcuate projection slidable within a corresponding shaped enlarged cavity of an arcuate slot, and being constrained to fore and aft arcuate displacement with respect to the upper portion, simultaneously in:
        i) a downward and forward direction in which the toe section pivots downward and the heel portion simultaneously displaces forward with respect to the attachment member; and
        ii) a rearward and upward direction in which the toe section pivots upward and the heel portion simultaneously displaces rearward with respect to the attachment member;
    c) an actuator, operatively coupled to the attachment member and the foot member, to move the attachment member and the foot member with respect to one another;
    d) a sensor, associated with the attachment member or the foot member, to sense frequency of contact, force of contact, or orientation of the attachment member or the foot member, and to output a corresponding output signal; and
    e) a controller, coupled to the actuator and the sensor, to process the output signal of the sensor and engage the actuator in response to the output signal.

11. A device in accordance with claim 10, wherein the controller automatically drives the actuator to move the foot member to a predetermined initial position in response to a predetermined signal from the sensor.

12. A device in accordance with claim 10, wherein the controller further comprises:
   a user input interface, configured to allow a user to program the controller to adjust the foot member to a position corresponding to changes in slope.

13. A device in accordance with claim 10, wherein the controller has a walk mode to respond to a relatively lower frequency and force of impact on the foot member, and a run mode to respond to a relatively higher frequency and force of impact on the foot member.

14. A device in accordance with claim 10, wherein the controller has:
   i) a downhill mode to move the foot member to a forward and downward position corresponding to walking down hill;
   ii) an uphill mode to move the foot member to a rearward and upward position corresponding to walking up hill; and
   iii) a level mode to move the foot member to a relatively level position for walking on relatively level terrain.

15. A device in accordance with claim 10, further comprising:
   means for a user to manually control the actuator.

16. A device in accordance with claim 10, wherein the foot member is constrained to fore and aft arcuate displacement with respect to the attachment member between at least two fixed positions, including:
   a) a low position, in which the heel section is disposed at a lower elevational position, and in which the heel section is disposed in a rearward position; and
   b) a high position, in which the heel section is disposed at a higher elevational position, and in which the heel section is disposed in a forward position.

17. A device in accordance with claim 10, wherein the arcuate slot has a T-shaped cross-sectional shape; and wherein the arcuate projection has a T-shaped cross-sectional shape.

* * * * *